US008877808B2

(12) United States Patent
McGeer et al.

(10) Patent No.: US 8,877,808 B2
(45) Date of Patent: *Nov. 4, 2014

(54) PROTECTION AGAINST SKIN DISEASES BY AURIN TRICARBOXYLIC ACID AND ITS DERIVATIVES

(71) Applicant: Aurin Biotech Inc., Vancouver (CA)

(72) Inventors: Patrick L. McGeer, Vancouver (CA);
Moonhee Lee, Vancouver (CA);
Douglas N. Bell, Rancho Mirage, CA (US)

(73) Assignee: Aurin Biotech Inc. (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/694,484

(22) Filed: Dec. 6, 2012

(65) Prior Publication Data

US 2014/0163106 A1   Jun. 12, 2014

(51) Int. Cl.
*A61K 31/235* (2006.01)
*A61K 31/19* (2006.01)
*A61K 31/194* (2006.01)

(52) U.S. Cl.
CPC .................................. *A61K 31/194* (2013.01)
USPC .......................................... 514/533; 514/568

(58) Field of Classification Search
USPC ................................................ 514/533, 568
See application file for complete search history.

(56) References Cited

U.S. PATENT DOCUMENTS

| 4,007,270 | A | 2/1977 | Bernstein et al. |
| 5,030,442 | A | 7/1991 | Uster |
| 6,770,633 | B1 * | 8/2004 | Robbins et al. ............. 514/44 R |
| 2013/0035388 | A1 | 2/2013 | McGeer |
| 2013/0035392 | A1 | 2/2013 | McGeer |

FOREIGN PATENT DOCUMENTS

| CA | 2388924 A1 | 5/2001 |
| EP | 0699070 B1 | 9/2002 |
| WO | 2001057184 A | 8/2001 |
| WO | 2010042728 A1 | 4/2010 |

OTHER PUBLICATIONS

Go'rrnicki et al. (J. Dermatological Science 27 (2001) 27-30).*
Health Issue (2010) 2 pages.*
Ballanti, E., et al., "Role of the complement system in rheumatoid arthritis and psoriatic arthritis: relationship with anti-TNF inhibitors", Autoimmun Rev: 2011, 10(10):617-623.
Cushman, M., et al., "Synthesis of the covalent hydrate of the incorrectly assumed structure of aurin tricarboxylic acid (ATA)", Tetrahedron, 1990, 46:1491-1498.
Garza, L.A., et al., "Prostaglandin D2 inhibits hair growth and is elevated in bald scalp of men with androgenic alopecia", Sci Transl Med, 2012, 4(126ra34):1-10.
Gemmer, C.M., et al., "Fast, noninvasive method for molecular detection and differentiation of *Malassezia* yeast species on human skin and application of the method to dandruff microbiology", J Clin Microbiol, 2002, 40(9): 3350-3357.
Gonzales, R.G., et al., "Fractionation and structural elucidation of the active components of aurin tricarboxylic acid, a potent inhibitor of protein nucleic acid interactions", Biochim Biophys Acta, 1979, 562(3):534-545.
Harries, M.J., et al., "Hair loss as a result of cutaneous autoimmunity: frontiers in the immunopathogenesis of primary cicatricial alopecia", Autoimmunity Reviews, 2009, 8(6):478-483.
Harries, M.J., et al., "Does collapse of immune privilege in the hair-follicle bulge play a role in the pathogenesis of primary cicatricial alopecia?", Clin Exp Dermatol, 2010, 35(6):637-644.
Hillmer, A.M., et al., "Genetic variation in the human androgenic receptor gene is the major determinant of common early-onset androgenic alopecia", Am J Hum Gen, 2005, 77(1):140-148.
Kawana, S., et al., "Deposition of the membrane attack complex of complement in pemphigus vulgaris and pemphigus foliaceus skin", J Investig Dermatol, 1989, 92(4):588-592.
Kerr, K, et al., "Epidermal changes are associated with symptomatic resolution of dandruff: biomarkers of scalp health", Int J Dermatol, 2011, 50(1):102-113.
Kotnik, V, "Complement in skin diseases", 2011, Acta Dermatoven APA, 20(1):3-11.
Lapidus, M., et al., "New inhibitors of complement fixation", Immunopharmacology, 1981, 3(2):137-145.
Lee, M, et al., "Selective inhibition of the membrane attack complex of complement by low molecular weight components of the aurin tricarboxylic acid complex", Neurobiol Aging, 2012, 33(10):2237-2246.
Lee, M., et al., "Aurin tricarboxylic acid self-protects by inhibiting aberrant complement activation at the C3 convertase and C9 binding stages", Neurobiol Aging, 2013, 34(5):1451-1461.
Meyer, K.C., et al., "Evidence that the bulge region is a site of relative immune privilege in human hair follicles", Br J Dermatol, 2008, 159(5):1077-1085.
Mills, K.J., et al., "Dandruff/seborrhoeic dermatitis is characterized by an inflammatory genomic signature and possible immune dysfunction: transcriptional analysis of the condition and treatment effects of zinc pyrithione", Br J Dermatol, 2012,166(Suppl 2):33-40.
Pfaltz, K., et al., "C3d immunohistochemistry on formalin-fixed tissue is a valuable tool in the diagnosis of bullous pemphigoid of the skin", J Cutan Pathol, 2010, 37(6):654-658.
Prodi, D.A., et al., "EDA2R is associated with androgenic alopecia", J Inves Derm, 2008,128(9):2268-2270.
Schwartz, J.R., et al., "A comprehensive pathophysiology of dandruff and seborrheic dermatitis-towards a more precise definition of scalp health", Acta Derm Venereol, 2013, 93:131-137.
Seah, P.P., et al., "Alternate-pathway complement fixation by IgA in the skin of dermatitis herpetiformis", The Lancet, 1973, 302(7822):175-177.
Tagami, "The role of complement-derived mediators in inflammatory skin diseases", Archives in Dermatological Research, 1992, 284(1):52-59.
Triolo, G, et al., "Impaired expression of erythrocyte glycolphosphotidylinosotol-anchored membrane CD59 in patients with psoriatic arthritis. Relation to terminal complement pathway activation", Clin Exp Rheumatol, 2003, 21(2):225-228.

* cited by examiner

*Primary Examiner* — Shirley V Gembeh

(74) *Attorney, Agent, or Firm* — Berliner & Associates

(57) ABSTRACT

This invention describes a method of preventing and treating inflammatory skin diseases by topical application of aurin tricarboxylic acid and its derivatives. Such diseases are characterized by immune attack, especially involving aberrant complement activation. The diseases include, but are not limited to, androgenetic alopecia (baldness), seborrheic dermatitis/dandruff, allergic dermatitis, primary cicatricial alopecia, pemphigus, psoriasis, discoid lupus erythematosis, and dermatitus herpetiformis.

19 Claims, 1 Drawing Sheet

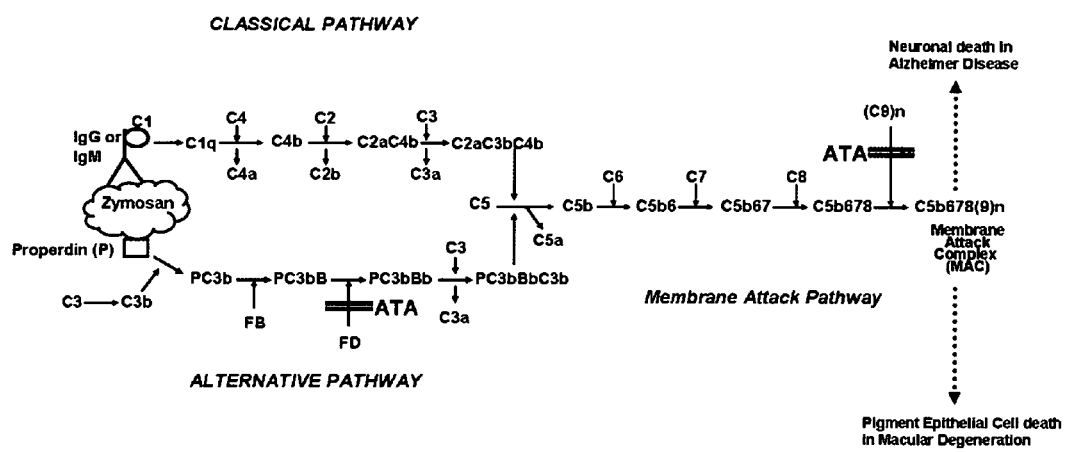

PROTECTION AGAINST SKIN DISEASES BY AURIN TRICARBOXYLIC ACID AND ITS DERIVATIVES

REFERENCES

Patent Documents
U.S. Pat. No. 4,007,270
U.S. Pat. No. 5,030,442
PCT/IB2012/053608
U.S. patent application Ser. No. 13/195,216
EP0699070

OTHER PUBLICATIONS

Ballanti E, et al. 2011. Role of the complement system in rheumatoid arthritis and psoriatic arthritis: relationship with anti-TNF inhibitors. Autoimmun Rev 10(10), 617-623.

Cushman M, Kanamathareddy S, 1990. Synthesis of the covalent hydrate of the incorrectly assumed structure of aurin tricarboxylic acid (ATA). Tetrahedron 46, 999-1010.

Garza L A, et al., 2012. Prostaglandin D2 inhibits hair growth and is elevated in bald scalp of men with androgenic alopecia. Sci Transl Med 4 (126).

Gemmer C M et al. 2002. Fast, noninvasive method for molecular detection and differentiation of Malassezia yeast species on human skin and application of the method to dandruff microbiology. J Clin Microbiol 40(9), 3350-3357.

Gober M D, Gaspari A A 2008. Allergic contact dermatitis. Curr. Dir. Autoimmun. 10, 1-26.

Gonzales R G, et al. 1979. Fractionation and structural elucidation of the active components of aurin tricarboxylic acid, a potent inhibitor of protein nucleic acid interactions. Biochim Biophys Acta 563, 534-545.

Harries M J, Meyer K C, Paus R. 2009. Hair loss as a result of cutaneous autoimmunity: frontiers in the immunopathogenesis of primary cicatricial alopecia. Autoimmune Rev. 8(6), 478-483.

Harries M J, et al. 2010. Does collapse of immune privilege in the hair-follicle bulge play a role in the pathogenesis of primary cicatricial alopecia? Clin. Exp. Dermatol. 35(6), 637-644.

Hillmer A M, et al. 2005. Genetic variation in the human androgenic receptor gene is the major determinant of common early-onset androgenic alopecia. Am. J. Hum. Gen., 77(1), 140-148.

Kawana S, et al. 1989. Deposition of the membrane attack complex of complement in pemphigus vulgaris and pemphigus foliaceus skin. J Investig Dermatol 92(4), 588-592.

Kerr K, et al. 2011 Epidermal changes are associated with symptomatic resolution of dandruff: biomarkers of scalp health. Int J Dermatol 50(1), 102-113

Kotnik V, 2010. Complement in skin diseases. Acta Dermatoven APA 19(1), 3-11.

Lee M, et al. 2012a. Selective inhibition of the membrane attack complex of complement by low molecular weight components of the aurin tricarboxylic acid complex. Neurobiol. Aging 33, 2237-2246.

Lee M, et al. 2012b. Aurin tricarboxylic acid self-protects by inhibiting aberrant complement activation at the C3 convertase and C9 binding stages. Neurobiol. Aging http://dx.doi.org/10.1016/j.neurobiolaging.2012.10.023

Meyer K C, et al. 2008. Evidence that the bulge region is a site of relative immune privilege in human hair follicles. Br J Dermatol. 159(5), 1077-1085.

Mills K J, et al. 2012. Dandruff/seborrhoeic dermatitis is characterized by an inflammatory genomic signature and possible immune dysfunction: transcriptional analysis of the condition and treatment effects of zinc pyrithione. Br J Dermatol. 166 Suppl 2, 33-40.

Pfaltz K, et al. 2010. C3d immunohistochemistry on formalin-fixed tissue is a valuable tool in the diagnosis of bullous pemphigoid of the skin. J Cutan Pathol 37(6), 654-658.

Prodi D A, et al. 2008. EDA2R is associated with androgenic alopecia. J Inves Derm. 128, 2268-2270.

Seah P P, et al. 1973. Alternate-pathway complement fixation by IgA in the skin of dermatitis herpetiformis. The Lancet Jul. 28, 1973, 175-177.

Schwartz J R, et al. 2012. A comprehensive pathophysiology of dandruff and seborrheic dermatitis-towards a more precise definition of scalp health. Acta Derm Venereol August 6 doi. 2340/00015555-1382

Triolo G, et al. 2003. Impaired expression of erythrocyte glycol-phosphotidylinosotol-anchored membrane CD59 in patients with psoriatic arthritis. Relation to terminal complement pathway activation. Clin Exp Rheumatol 21, 225-228.

FIELD OF THE INVENTION

This invention pertains to the use of low molecular weight components of the aurin tricarboxylic acid synthetic complex and their derivatives, to treat skin conditions where self damage is caused by aberrant complement activation.

BACKGROUND OF THE INVENTION

Skin is the outer covering of mammals which protects all the deeper layers of the body. As such, it is equipped with a powerful immune system to ward off challenges from the external environment. Complement is a vital component of that immune protection. However, it is a two edged sword because aberrant activity can also damage host tissue. This is particularly true of the membrane attack complex (MAC) which can cause bystander lysis of host cells. Therefore agents that can appropriately inhibit aberrant complement activation will have important therapeutic benefits in skin disorders where self damage occurs.

Complement is activated through two major pathways, the classical and the alternative. For a summary of the complement pathways, and the stages inhibited by the invention described here, see Drawing 1.

Bernstein et al. in U.S. Pat. No. 4,007,270 claimed that aurin tricarboxylic acid was a complement inhibitor. However no chemical analysis of the claimed product was carried out. Subsequent analytical studies based on the synthetic method described in the patent showed that the products consisted mostly of a mixture of high molecular weight materials of uncertain structure (Gonzalez et al. 1978; Kushman and Kanamathareddy 1990; Lee et al. 2012a; PCT/IB2012/053608; U.S. patent application Ser. No. 13/195,216). Moreover, these high molecular weight components have powerful side effects which would render them unsuitable for human administration, including inhibition of protein nucleic acid interactions (Gonzales et al. 1979).

It has previously been demonstrated that aurin tricarboxylic acid itself (ATA), and the closely related derivatives aurin quadracarboxylic acid (AQA), and aurin hexacarboxylic acid (AHA), block classical pathway formation at the stage of C9 binding to C5b678 so that formation of the MAC (C5b-9) cannot take place (Lee at al. 2012a). It has further been demonstrated that ATA binds to Factor D, the protease which cleaves membrane bound Factor B. This creates a block in the alternative pathway subsequent to the stage where properdin (Factor) P has bound C3b and Factor B to form the complex PC3bB. Cleavage of Factor B by Factor D to form PC3bBb (C3 convertase) is required for the pathway to proceed. Therefore ATA also blocks the alternative pathway at the C3 convertase stage (Lee et al. 2012b).

The invention described here is novel in that it utilizes low molecular weight components of the aurin tricarboxylic acid complex (ATAC) to block complement activation in the skin. These include aurin tricarboxylic acid itself (ATA, MW 422), aurin quadracarboxylic acid (AQA, MW 573) and aurin hexacarboxylic acid (AHA, MW 857). These active molecules can be isolated from the mixture obtained after synthesis by the method of Cushman and Kanamathareddy (1990) by passing the crude synthetic product through a 1 kDa filter. They occur in the approximate proportion of 78% AHA, 15% AQA, and 7% AHA.

ATA itself, or the complex ATAC, by inhibiting complement activation, can be expected to treat successfully many skin diseases where aberrant complement activation is reported to occur (Kotnick 2010). Although the causes of such activation may be diverse, the fundamental reactions are common. They involve activation of local phagocytes, release of cytotoxins and inflammatory mediators, and formation of the autolytic MAC. Therefore, ATA and its derivatives will be successful in treating these diverse conditions by inhibiting unwanted complement activation at the C3 convertase and C9 addition to C5b-8 stages.

Pemphigus is one example. In this potentially fatal disorder, there is an autoimmune attack against desmoglien, the adhesive protein which forms the attachment of adjacent epidermal cells. The classical and alternative pathways are both activated with consequent formation of the membrane attack complex (Kawana et al. 1989), indicating that ATA and its derivatives will be effective therapeutic agents.

Dermatitis herpetiformis is a condition which is characterized by an extremely itchy rash. It is linked to gluten intolerance and immune attack against the protein epidermal transglutaminase (Preisz et al. 2005). The lesions are characterized by depositions of IgA accompanied by C3, Factor P and Factor B, indicating activation of the alternative pathway of complement (Seah et al. 1973). By inhibiting the alternative pathway at both the C3 convertase and C9 addition stages, ATA and its derivatives will be effective therapeutic agents.

Psoriasis is a common skin condition which is characterized by an immune response. There is a proliferation of keratinocytes which release inflammatory cytokines such as TNFα, as well as the complement proteins C3, Factor B, C7, and C9 (Ballantini et al. 2011). Since TNFα increases C9 synthesis, it contributes to formation of the membrane attack complex (Kotnik 2010). Specifically, it has been shown that there is deficiency in psoriatic arthritic patients of membrane bound CD59, the protective agent against self attack by the MAC (Triolo et al. 2003). Therefore ATA and its derivatives will be effective therapeutic agents.

Discoid lupus erythematosis is an autoimmune disorder which is highly exacerbated by sunlight. It is currently treated with topical steroids, indicative of the effectiveness of immune blockade. By blocking aberrant complement activation, ATA and its derivatives will be effective therapeutic agents.

Irritant or allergic dermatitis occurs when the immune system of the skin attacks an allergen or other irritant. Keratinocytes can become damaged by this excessive attack. Aberrant complement activation will be ameliorated by treatment with ATA and its derivatives.

Primary cicatricial alopecia (PCA) is a skin disorder in which epithelial hair follicle stem cells are damaged or destroyed by inflammatory events (Harries et al. 2009). The affected stem cells reside in the outer root sheath of hair follicle bulges (Harries et al. 2009). This is an area hypothesized to be immunologically privileged (Meyer et al. 2008). Loss of such immunological privilege results in immune attack, so that hair follicles are replaced by scar tissue, with loss of hair (Harries et al. 2010). A mainstay of treatment is topical steroids. Since inflammation activates the complement system. By blocking this aberrant complement activation, ATA and its derivatives will be effective therapeutic agents.

Androgenic alopecia (baldness) is the most common form of hair loss in males. It begins after puberty, with initial losses occurring in the temporal and occipital areas. It typically advances to baldness covering the entire scalp except for a rim extending around the peripheral regions. The cause is generally acknowledged to be a vulnerability of hair follicles in these areas to androgens, particularly dihydrotestosterone (DHT) (Garza et al. 2012). DHT interacts with the androgen receptor (AR) and it is high levels of this receptor that are presumed to create the vulnerability. The gene for AR is located at Xq11-Xq12. Genetic analyses have shown that variants in the receptor are associated with androgenic alopecia (Hillmer et al. 2005) and especially with a nearby gene named ectodysplasin receptor 2A (EDA2R) (Prodi et al. 2008). The product of the gene is a transmembrane protein of the tumor necrosis factor receptor superfamily. To date there is no explanation as to why activation of these receptors by DHT should result in disappearance of hair follicles in androgenic alopecia. Treatments for baldness have been developed based on reducing the substrate for these receptors, or increasing scalp circulation. Examples include minoxidil, an arterial dilator that has been used systemically and topically to promote hair growth (U.S. Pat. No. 5,030,442). Finasteride, which blocks 5-alpha reductase conversion of testosterone to DHT, has been approved for hair loss. However, none of these approaches, or others that are totally empirical, provide any insight as to the mechanism that actually causes disappearance of hair follicles. Nevertheless, we have demonstrated in this invention that ATA and its derivatives not only arrest hair loss, they stimulate the reappearance of hair follicles with new hair growth in areas that have become bald. Application of ATA at a concentration of 1-5 micrograms per ml 2-3 times daily, results in an abundance of new hair follicles appearing in previously bald areas after 4-6 weeks of treatment. This indicates that baldness can to some degree reflect hair follicle suppression rather than hair follicle destruction. One possible explanation is that ATA and its derivatives are blocking complement attack of an enduring nature, thus permitting keratinocyte follicular re-growth.

Seborrheic dermatitis and dandruff are caused by an excessive loss of corneocytes from the outer layer of the epidermis. Immune dysfunction is suspected (Mills et al. 2012). The corneocytes adhere to each other creating flakes which are then shed. The pathogenesis appears to result from interactions between scalp skin, cutaneous microflora and the cutaneous immune system (Kerr et al. 2011). A proposed cause is Malassezia fungi (Gemmer et al. 2002). Increased levels of inflammatory markers are detected in biopsy specimens including IL-1α and IL-1RA (Kerr et al. 2011). By blocking the consequent complement activation, ATA and its derivatives will be effective therapeutic agents.

Alopecia areata is a condition in which there is hair loss, usually from the scalp. It is characterized by a lymphocytic infiltration around vulnerable follicles, so that the hair growth disappears. However there may be remissions so that hair may grow again. The standard treatment is topical corticosteroids appropriate to an inflammatory response, or minodoxil, a capillary dilator which stimulates hair growth. By blocking the complement activation which accompanies inflammation, ATA and its derivatives will be effective therapeutic agents.

SUMMARY OF THE INVENTION

This invention describes a method of preventing and treating inflammatory skin diseases by topical application of aurin tricarboxylic acid and its derivatives. Such diseases are characterized by immune attack, especially involving aberrant complement activation. The diseases include, but are not limited to, androgenetic alopecia (baldness), seborrheic dermatitis/dandruff, allergic dermatitis, primary cicatricial alopecia, pemphigus, psoriasis, discoid lupus erythematosis and dermatitus herpetiformis.

The application may be as a spray with the active agents being dissolved in water or a suitable buffer. The application may also be in the form of an ointment, gel, or shampoo, with the active ingredients being dissolved in an appropriate vehicle. Examples of such vehicles are glycerine as a gel, Alopecia Vera as an ointment, and sodium lauryl sulfate plus cocamidopropyl betaine as a shampoo.

DETAILED DESCRIPTION OF A PREFERRED EMBODIMENT OF THE INVENTION

The invention described here can be applied using ATA, or any combination of ATA, AQA and AHA as the active materials. These ingredients have almost identical actions in blocking complement activation, so there is no preference for any of them based on its activity or mechanism of action. The synthetic procedure described above will produce a mixture of products. The low molecular weight ingredients must be separated by filtration or an equivalent technique. If a cutoff filter of 500 Da is used, the active material in the filtrate will be ATA. If a 1 kDa cutoff filter is used, the active material will be a combination of ATA, AQA and AHA in the approximate ratio of 78:15:7. The latter is referred to as ATAC (aurin tricarboxylic acid complex).

As a preferred embodiment, ATA or ATAC can be dissolved in aqueous solution over a wide range of concentrations. Optimum values vary between 1-10 milligrams per ml. The aqueous solution can then be directly applied as a spray or by other methods to the affected skin area.

For longer acting purposes, the aqueous solution can be added to any standard ointment in a 1:1 or other suitable ratio. Glycerine is one example of a suitable ointment. The ointment can then be rubbed over the affected skin area.

For even longer acting purposes, the aqueous solution can be added in a 1:1 or other suitable ratio to any standard gel. Aloe Vera is one example of a standard gel. The gel can then be rubbed over the affected skin area.

For scalp cleansing, especially in cases of dandruff/seborrheic dermatitis, the aqueous solution can be added in a 1:1 ratio to a shampoo base consisting of sodium lauryl sulfate plus cocamidopropyl betaine.

As those skilled in the art will know, these diseases are only examples of many that may be found where the invention described here will have therapeutic benefit.

DESCRIPTION OF DRAWING

1. Schematic diagram of both the classical and alternative complement pathways. Zymosan is a well known activator of both the classical and alternative pathways. ATA and its derivatives block formation of the membrane attack complex in both these pathways by binding to C9, thus preventing it from attaching to membrane bound C5b-8. ATA and its derivatives also block the alternative pathway by binding to Factor D, thus preventing it from cleaving the membrane bound complex PC3bB to form the C3 convertase enzyme PC3bBb.

What is claimed is:

1. A method of treating skin diseases and disorders in a human or animal in need thereof comprising inhibiting complement activation by topical application of a therapeutically effective amount of aurin tricarboxylic acid (ATA), aurin quadracarboxylic acid (AQA), aurin hexacarboxylic acid (AHA), or a combination thereof, as an active agent for treatment of the skin diseases and disorders selected from the group consisting of androgenetic alopecia, alopecia areata, seborrheic dermatitis or dandruff, irritant dermatitis, primary cicatricial alopecia, pemphigus, psoriasis, discoid lupus erythematosis and dermatitis herpetiformis, wherein the active agent excludes any components greater than 1 kDa.

2. A method as claimed in claim 1 where the condition is androgenetic alopecia.

3. A method as claimed in claim 1 where the condition is alopecia areata.

4. A method as claimed in claim 1 where the condition is primary cicatricial alopecia.

5. A method as claimed in claim 1 where the condition is dandruff/seborrheic dermatitus.

6. A method as claimed in claim 1 where the condition is irritant dermatitis.

7. A method as claimed in claim 1 where the condition is pemphigus.

8. A method as claimed in claim 1 where the condition is psoriaris.

9. A method as claimed in claim 1 where the condition is dermatitis herpetiformis.

10. A method as claimed in claim 1 where the condition is discoid lupus erythematosis.

11. A method as claimed in claim 1 where a spray containing the active agent at a concentration varying between 0.1-100 mg per ml is applied.

12. A method as claimed in claim 1 where a gel containing the active agent at a concentration varying between 0.1-100 mg per ml is applied.

13. A method as claimed in claim 1 where an ointment containing the active agent at a concentration varying between 0.1-100 mg per ml is applied.

14. A method as claimed in claim 1 where a shampoo containing the active agent at a concentration varying between 0.1-100 mg per ml is applied.

15. A method as claimed in claim 1 wherein the active agent is ATA.

16. A method as claimed in claim 1 wherein the active agent is AQA.

17. A method as claimed in claim 1 wherein the active agent is AHA.

18. A method as claimed in claim 1 wherein the active agent is a combination of ATA, AQA and AHA.

19. A method as claimed in claim 18 wherein the combination of ATA, AQA and AHA is an approximate ratio of 78:15:7.

* * * * *